(12) United States Patent
McGinnis et al.

(10) Patent No.: US 6,377,052 B1
(45) Date of Patent: *Apr. 23, 2002

(54) MONITORING FLUID CONDITION THROUGH AN APERTURE

(75) Inventors: Peter J. McGinnis, Brookfield; Paul G. Rops, Germantown; Mark H. Polczynski, Elm Grove; Francis C. Edrozo; Richard W. Hirthe, both of Milwaukee; Steven R. Schachameyer, Whitefish Bay; Lian Q. Zou, Shorewood, all of WI (US)

(73) Assignee: Eaton Corporation, Cleveland, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/433,495

(22) Filed: Nov. 3, 1999

(51) Int. Cl.$^7$ ........................ G02N 27/02; G02N 27/07

(52) U.S. Cl. ...................... 324/446; 324/439; 324/693; 324/698; 324/724

(58) Field of Search ................................ 324/439, 446, 324/647, 691, 693, 698, 705, 707, 722, 724, 71.1

(56) References Cited

U.S. PATENT DOCUMENTS

| | | | | |
|---|---|---|---|---|
| 3,569,824 A | * | 3/1971 | Ruse | 324/439 |
| 3,686,926 A | * | 8/1972 | Miller et al. | 324/698 X |
| 3,970,925 A | | 7/1976 | Procter et al. | 324/57 Q |

(List continued on next page.)

FOREIGN PATENT DOCUMENTS

| | | |
|---|---|---|
| DE | 19808940 | 10/1998 |
| GB | 2 306 660 | 7/1997 |
| GB | WO 98/46985 | 10/1998 |

OTHER PUBLICATIONS

"The Applications of AC Impedance Technique For Detecting Glycol Contamination in Engine Oil" by S.S.Wang, et al., published Jan. 4, 1997 by Elselvier Science S.A.

"Novel Sensors for Portable Oil Analyzers" 1998 (no month) Case Western Reserve University, Cleveland, Ohio Dept. of Physics NTIS 19980624 080.

(List continued on next page.)

*Primary Examiner*—Glenn W. Brown
(74) *Attorney, Agent, or Firm*—Roger A. Johnston

(57) ABSTRACT

A method for real time monitoring fluid in a vessel with a probe having a pair of electrodes immersed in the fluid. The disclosed probe has the electrodes arranged helically on a rod, sized and configured for insertion in an engine dipstick hole. Preferably, the probe has spiral electrode winding up regions different pitch to provide improved impedance response at low fractional Hertz and high (at least one Hertz) frequencies of excitation. In one version with alternating voltage the difference in current magnitude measured at the low and high frequencies is compared with stored known values for known fluid conditions and an electrical signal indicative of fluid condition is generated. Examples with engine drain oil and heavy duty transmission lubricant fluid are presented. The impedance properties measured can determine the percentage remaining useful life (RUL) of the fluid. In another version of the method the current phase shift angle is measured at the fractional Hertzian frequency; and, from known values of current phase shift angle of the fluid, at various conditions, the condition of the fluid determined. The differential current measured and the measured phase shift angle may be combined, for example, by the square of the sum of the squares procedure to provide an enhanced impedance change indicator.

40 Claims, 15 Drawing Sheets

U.S. PATENT DOCUMENTS

| | | | |
|---|---|---|---|
| 4,165,641 A | 8/1979 | Pomerantz et al. | 73/290 R |
| 4,646,070 A | 2/1987 | Yasuhara et al. | 340/603 |
| 4,677,847 A | 7/1987 | Sawatari et al. | 73/64 |
| 4,733,556 A | 3/1988 | Meitzler et al. | 73/64 |
| 4,757,252 A | 7/1988 | Maltby et al. | 324/61 P |
| 5,274,335 A | 12/1993 | Wang et al. | 324/689 |
| 5,382,942 A | 1/1995 | Raffa et al. | 340/457.4 |
| 5,388,448 A * | 2/1995 | Showalter et al. | 324/693 X |
| 5,852,404 A * | 12/1998 | Amini | 324/698 X |
| 5,889,200 A | 3/1999 | Centers et al. | 73/53.01 |
| 6,278,281 B1 * | 8/2001 | Bauer et al. | 324/441 |

OTHER PUBLICATIONS

"AC Impedance Measurements of the Resistance and Capacitance of Lubricants" by S. S. Wang, et al, published Jun. 13, 1986 ASLE Transactions Vol. 30, 4, 436–443.

The Development of in situ Electrochemical Oil–Condition Sensors by S. S. Wang, et al., Published by Elsevier Sequoia 1994 (no month).

"Development of an Automatic Engine Oil–Change Indicator System" by Shirley E. Schwartz and Donald J. Smolenski, published Feb. 1987 Society of Automotive Engineers.

* cited by examiner

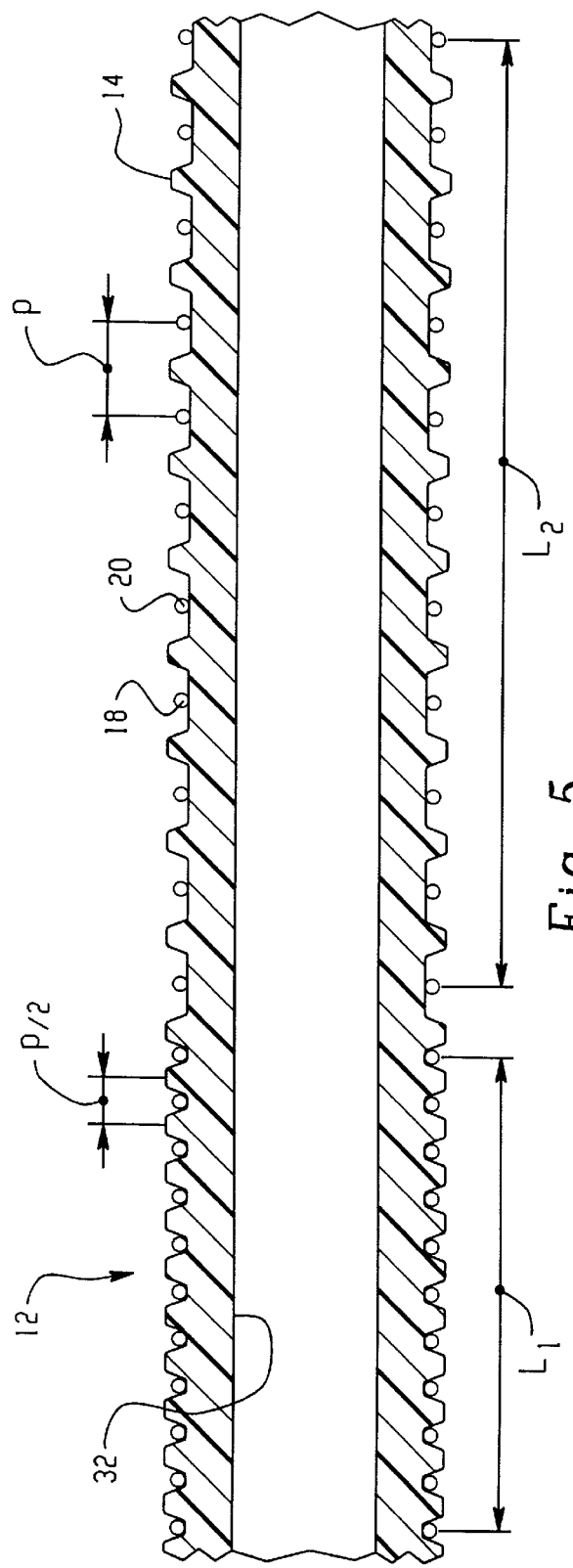
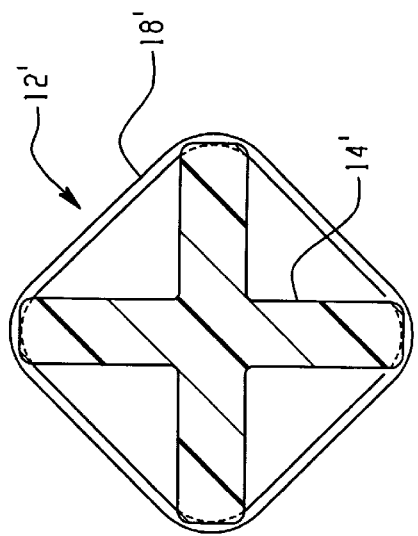
Fig. 5
Fig. 6

MONITORING FLUID CONDITION THROUGH AN APERTURE

BACKGROUND OF THE DISCLOSURE

The present invention relates to devices for continuously electrically monitoring the condition of a fluid in a vessel such as the condition of oil for lubricating and particularly the condition of crankcase or sump oil in an internal combustion engine or the lubricant in a power transmission device.

Shown and described in a copending application entitled "FLUID CONDITION MONITOR", Ser. No. 09/220,556 Filed Dec. 23, 1998 now U.S. Pat. No 6,278,281 in the names of Robert A. Bauer, Richard W. Hirthe, Mark H. Polczynski, Martin A. Seitz and James E. Hanson and assigned to the assignee of the present application is a device utilizing electro impedance spectroscopy techniques for monitoring in situ the condition of engine or transmission lubricant and providing an electrical indication of the condition. The device of the aforesaid patent application to Bauer, et al. describes measuring the electrical impedance of the fluid to be monitored at a first low frequency current and at a second high frequency current of at least one Hertz, computing the difference of the measured current as an analog of the impedances and comparing the computed difference with stored values for known fluid conditions to thereby determine the condition of the monitored fluid and to provide an electrical indication when the fluid condition reaches a predetermined threshold. The device of the aforesaid Bauer, et al. application describes a sensor probe having spaced parallel plates or interdigitated strips of a generally rectangular configuration disposed to extend from a plug or closure in the wall of the vessel containing the fluid. However, the disadvantage of the device described in the Bauer, et al. application is that the construction of the probe is difficult where a large plate area is required inasmuch as the spacing and area of the plates must be precisely controlled. The aforesaid Bauer, et al. device has the disadvantage of being bulky and somewhat cumbersome to install particularly in applications where the available access opening in the fluid vessel is small. Furthermore, the Bauer, et al. device has been found to be temperature dependant; and, it has been desired to achieve automatic temperature compensation or adjustment for the impedance measurements taken over the range of operating temperatures to which the fluid is exposed in service.

For motor vehicles in mass production it has long been desired to provide a way or means of continuously electrically monitoring in situ the condition of fluid in a vessel such as engine or transmission oil in the sump and to permit such monitoring to be accomplished in a way requiring no modification of the fluid vessel such as the engine block or crankcase or the transmission casing.

In addition, it has been desired to provide a way of predicting the Remaining Useful Life (RUL) of engine oil. Heretofore, it has been necessary to drain a sample of the engine oil and perform laboratory analyses, such as by High Pressure Differential Scanning Calorimetry (HPISC) to determine the amount of residual antioxidant components blended into the oil by the motor oil manufacturer. However, this is an expensive and time consuming procedure and can be performed only at selected intervals in the engine service life. Thus it has long been desired to provide a way or means of providing a vehicle on-board sensor capable of providing an electrical indication of the engine oil in real time.

BRIEF SUMMARY OF THE INVENTION

The present invention provides a solution to the above-described problem of enabling continuous electrical monitoring in situ of the condition of fluid in a vessel such as engine crankcase or power transmission oil by electro-impedance spectroscopy techniques employing sensing of the changes in impedance by current measurement as an analog thereof between a pair of spaced parallel conductors at a first sub-Hertzian (low) and a second Hertzian (high) frequency. The impedance is computed from current measurements and the computed impedance adjusted for temperature variation and the difference in the impedance computed and the difference compared with stored values of impedance as a function of temperature for known fluid or lubricant conditions to determine the instant fluid conditions; and, an electrical indication is provided when a threshold condition has been reached. The sensor of the present invention has sensed changes of impedance difference of the fluid of over seven hundred percent (700%) from new to fully depleted fluid such as engine oil, which provides a high resolution sensitivity of measurement.

Alternatively, the probe can be excited by a fractional or low frequency alternating voltage and at a high frequency of at least one Hertz and the phase shift of the resulting current at the high and low frequency determined by a zero crossing detector. The reactive impedance or reactance may then be computed and the differential reactance compared with known values to determine the fluid condition.

The monitor of the present invention includes a sensor probe having the conductors comprising wires disposed or wound spirally, preferably helically, on an elongated mandrel near the distal end. The spirally wound configuration is sized and configured to be insertable through an existing dipstick hole in the engine or transmission. The proximal end of the mandrel extends outwardly of the existing dipstick aperture and has a relatively small casing or housing thereon which has disposed therein the electronic circuitry for impedance current measurement and the determination of the fluid condition from stored values of such measurements in a look-up table and providing an electrical indication signal upon the fluid reaching a critical threshold condition. The fluid condition monitor of the present invention is particularly suitable to automotive applications wherein the probe inserted into a dipstick aperture in the engine may be connected to the vehicle power supply for providing the electrical indication to a remote indicator provided on the instrument cluster for display to the vehicle operator.

The spirally wound electrodes of the probe of the present invention are preferably wound in a particular pitch for an appropriate number of turns and then the pitch is reduced to about half for the remainder of turns to provide the desired length of the electrodes for the impedance measurement. The electrodes include lead means extending to the proximal end for connection to the circuitry externally of the dipstick aperture in the vessel containing the fluid to be monitored.

The present invention thus provides a unique electrical monitor for insertion in an existing fluid dipstick aperture which permits retrofitting in field service by simply removing the manual dipstick and inserting a probe through the dipstick aperture and connecting the probe to a suitable power supply for energizing the circuitry provided on the probe.

An RTD temperature sensor is included on the distal end of the probe for providing a temperature measurement of the fluid, which measurement is provided to the circuitry for providing a signal input for adjusting the impedance computed for measured current for temperature based on stored values or a known relationship established for variations in impedance of the electrodes in the fluid with temperature. The difference in the impedance computed at the fractional or low frequency and the high frequencies is then computed and a comparison is made with the known values of impedance difference as a function of temperature for known fluid conditions. If desired, a pair of self-heated thermistors may be disposed in spaced relationship on the probe for detecting a fluid level below the desired threshold and providing a low-fluid defeat input for disabling the fluid condition impedance measurements and providing a low-fluid indication.

BRIEF DESCRIPTION OF THE DRAWINGS

FIG. 5 is an enlarged view of a portion of FIG. 3;

FIG. 6 is a transverse section view of an alternate embodiment of the probe of the device of FIG. 1;

DETAILED DESCRIPTION OF THE PREFERRED EMBODIMENT

Figure 1:
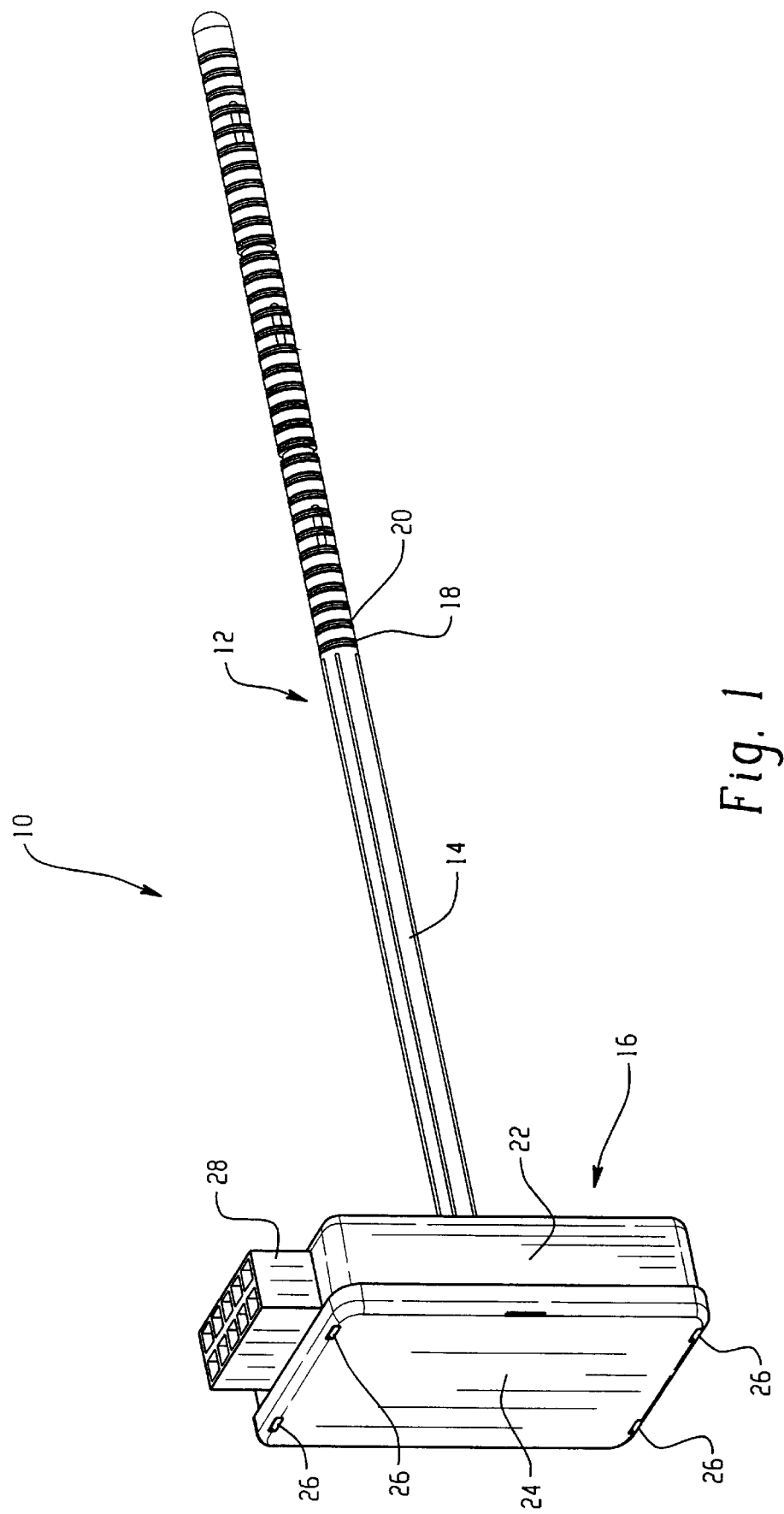
FIG. 1 is an isometric view of the monitor assembly of the present invention including the probe and the housing for the circuitry.

Referring to FIG. 1, the monitor of the present invention is indicated generally at 10 and includes a probe indicated generally at 12 comprising an elongated member or rod 14 preferably sized and configured for insertion into a dipstick aperture in a fluid vessel, such as an engine or power transmission, and includes a casing or housing indicated generally at 16 attached to the proximal end of the rod 14. Rod 14 has a plurality of spaced generally parallel electrodes 18, 20 disposed in spiral arrangement about the region adjacent the distal end of the rod 14.

Casing 16 includes a shell 22 having a cover 24 secured thereto, as for example, by snap locking engagement in slots 26 provided in the cover. Shell 22 has an electrical receptacle 28 extending from one side thereof which is adapted for connection to a multiple pin wiring harness connector.

Figure 2:
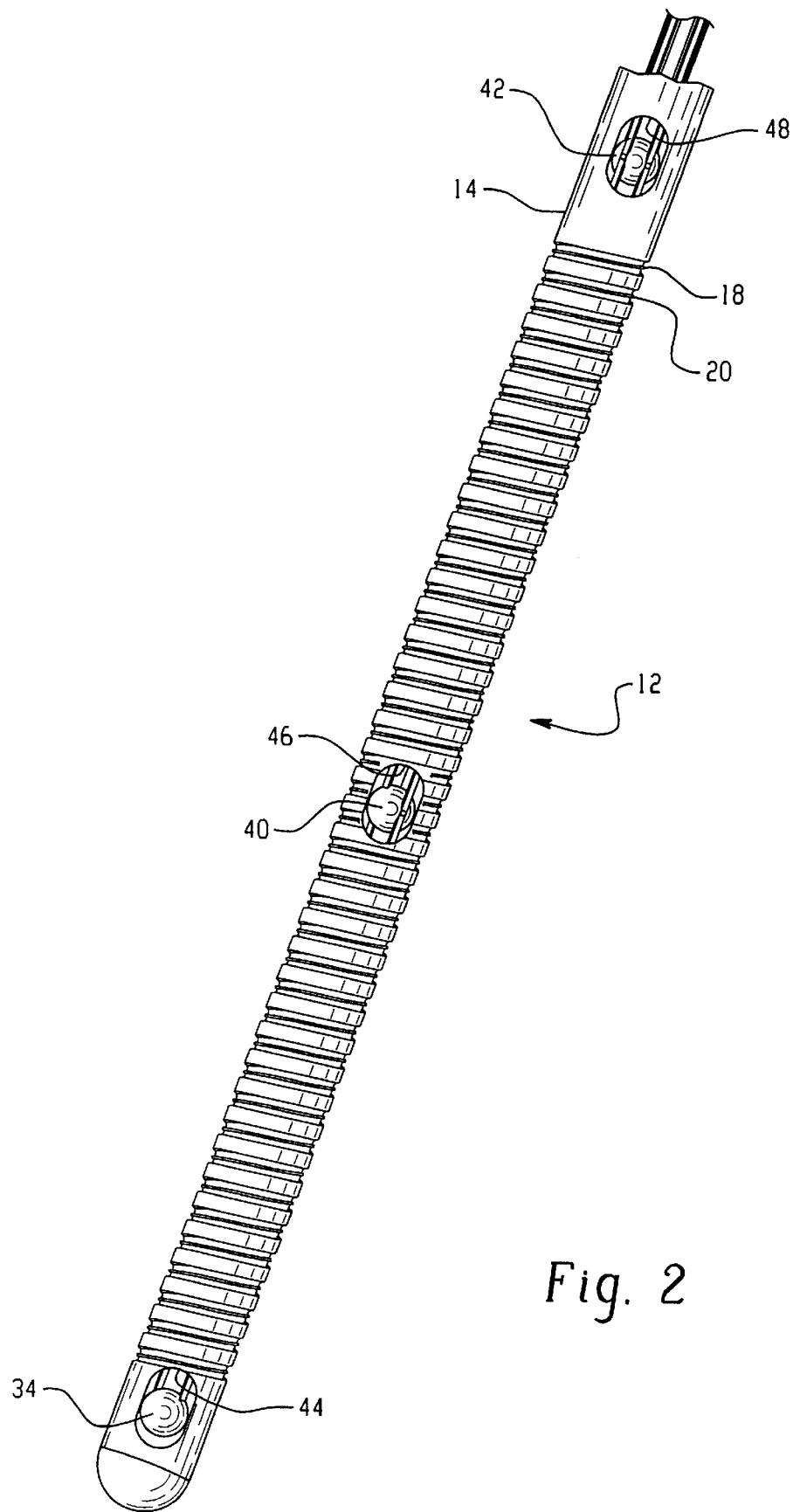
FIG. 2 is an enlarged view of a portion of the distal end of the probe of the device of FIG. 1.
Figure 3:
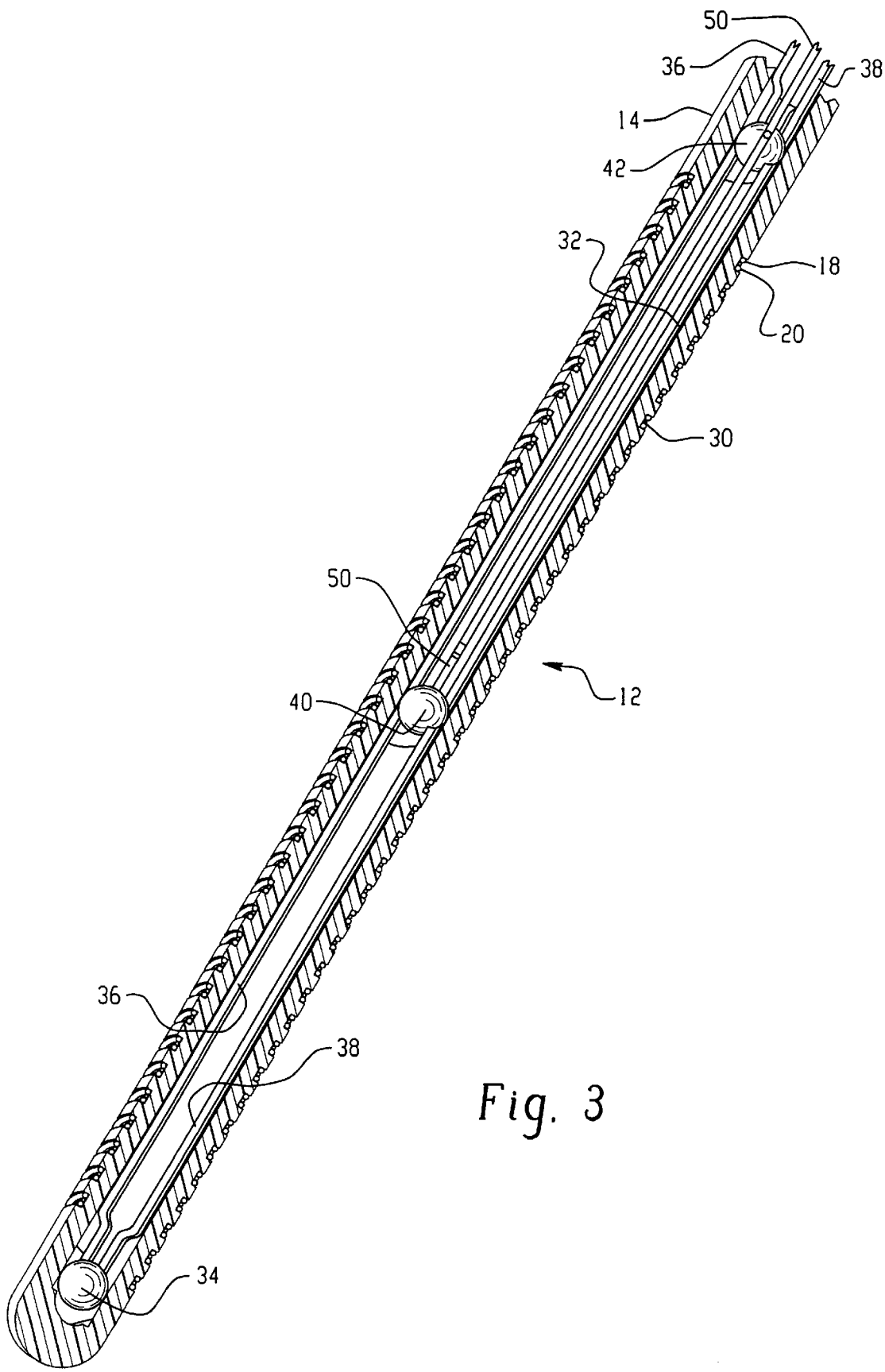
FIG. 3 is a view similar to FIG. 2 with a portion broken away.

Referring to FIGS. 2 and 3, probe 12 includes a spiral groove 30 formed thereon which has the electrodes 18, 20 received therein for controlling the spacing or pitch of the spiral or helical arrangement of the electrodes. In the present practice of the invention, rod 14 has a hollow 32 formed in the interior thereof and extending to the region of the distal end and has received therein a temperature sensing thermistor 34 which has a pair of electrical leads 36, 38 connected thereto and extending outwardly of the proximal end of the rod 14 for connection to the circuitry as will hereinafter be described.

If desired, optionally a pair of level sensing thermistors 40, 42 are received in the hollow 32 and located at suitable stations therealong so as to detect the presence of fluid thereon when the thermistors 40, 42 are self-heated in a manner known in the art.

Figure 4:
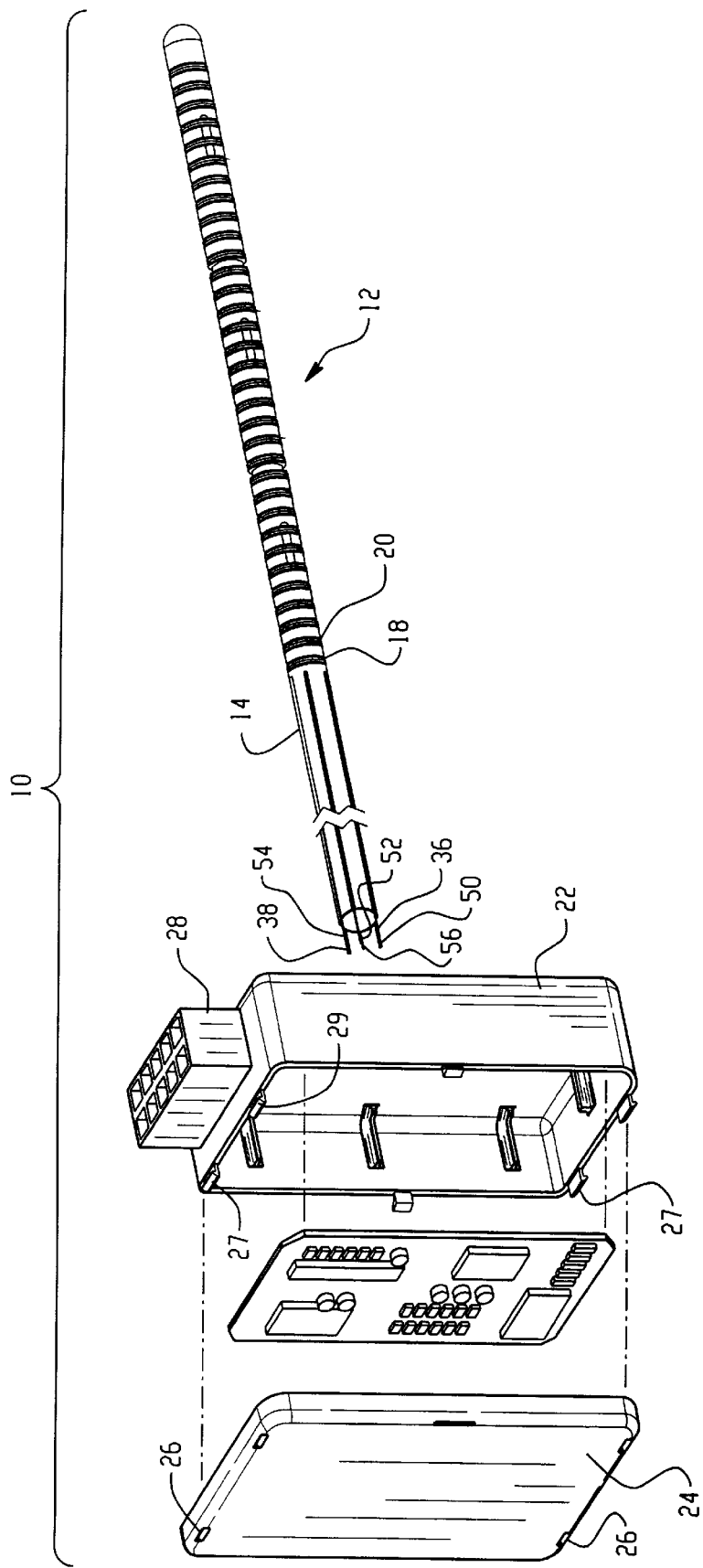
FIG. 4 is an exploded view of the device of FIG. 1.

As shown in FIG. 2, the thermistor 34 is exposed to the fluid in which the probe is to be immersed by a cut-out or aperture 44 provided in the rod 14; and, similarly thermistors 40, 42 are exposed to the fluid by cut-outs 46, 48. Thermistors 40, 42 also have electrical leads connected thereto and which extend outwardly of a proximal end of the rod 14 as denoted by reference numerals 50, 52, 54, 56 in FIG. 4.

A pair of electrical leads 58, 60 are connected to the electrodes 18, 20 and extend outwardly from the proximal end of the probe 14.

Referring to FIG. 5, the arrangement of the electrodes 18, 20 are shown in the preferred practice wherein the electrodes have a constant pitch spacing denoted by the reference character "p" for an axial distance denoted by the reference character $L_2$; and, have an increased pitch or decreased pitch spacing denoted by the reference character "½p" for an axial distance denoted by the reference character $L_1$. The portion of the spiral electrodes in the region $L_2$ provides improved sensitivity to the bulk impedance properties of the fluid at the higher frequencies of at least one Hertz; where as, the portion of the electrode in the region denoted $L_1$ provides imp roved sensitivity to the surface effects of the fluid on the conductors as measured at the lower or fractional Hertz frequencies.

In the present practice of the invention, a probe suitable for a dipstick application in an internal combustion engine has been satisfactorily made having a pitch diameter of about 0.25 inches (6.3 mm) formed of wire of about number 25 AWG (0.46 mm) diameter wire of non-magnetic material such as, for example, AISI type 303 stainless steel. The electrodes 18, 20 are spirally and preferably helically formed by winding over a rod 14 formed of suitable high dielectric material such as, for example polytetrafluoroethylene (PTFE) material. The electrodes are wound at a pitch spacing corresponding to the spacing "p" for the distance $L_2$ of about 4 inches (102 mm), with reference to FIG. 5, having about eight turns with a pitch spacing "p" of about 0.8 mm. The electrodes 18, 20 are wound for an additional length $L_1$ of about thirteen turns at a pitch spacing "½p" of about 28 mm for a distance $L_1$ of about 102 mm. However, it will be understood that the above-described dimensions for the wire diameter and pitch spacing and pitch diameter may be varied in accordance with the sensitivity, current carrying requirements and available space for winding for a particular application.

Referring to FIG. 6, an alternative embodiment of the probe 12' is shown wherein the rod 14' has a generally ribbed, and preferably cruciform, configuration in transverse section for supporting the electrode wires 18', 20'.

Although PTFE material has been found preferable, it will be understood that other materials may be used, as for example, polyphenylenesulfide or any other material stable in lubricating oil at temperatures up to about 150° C.

Figure 7:
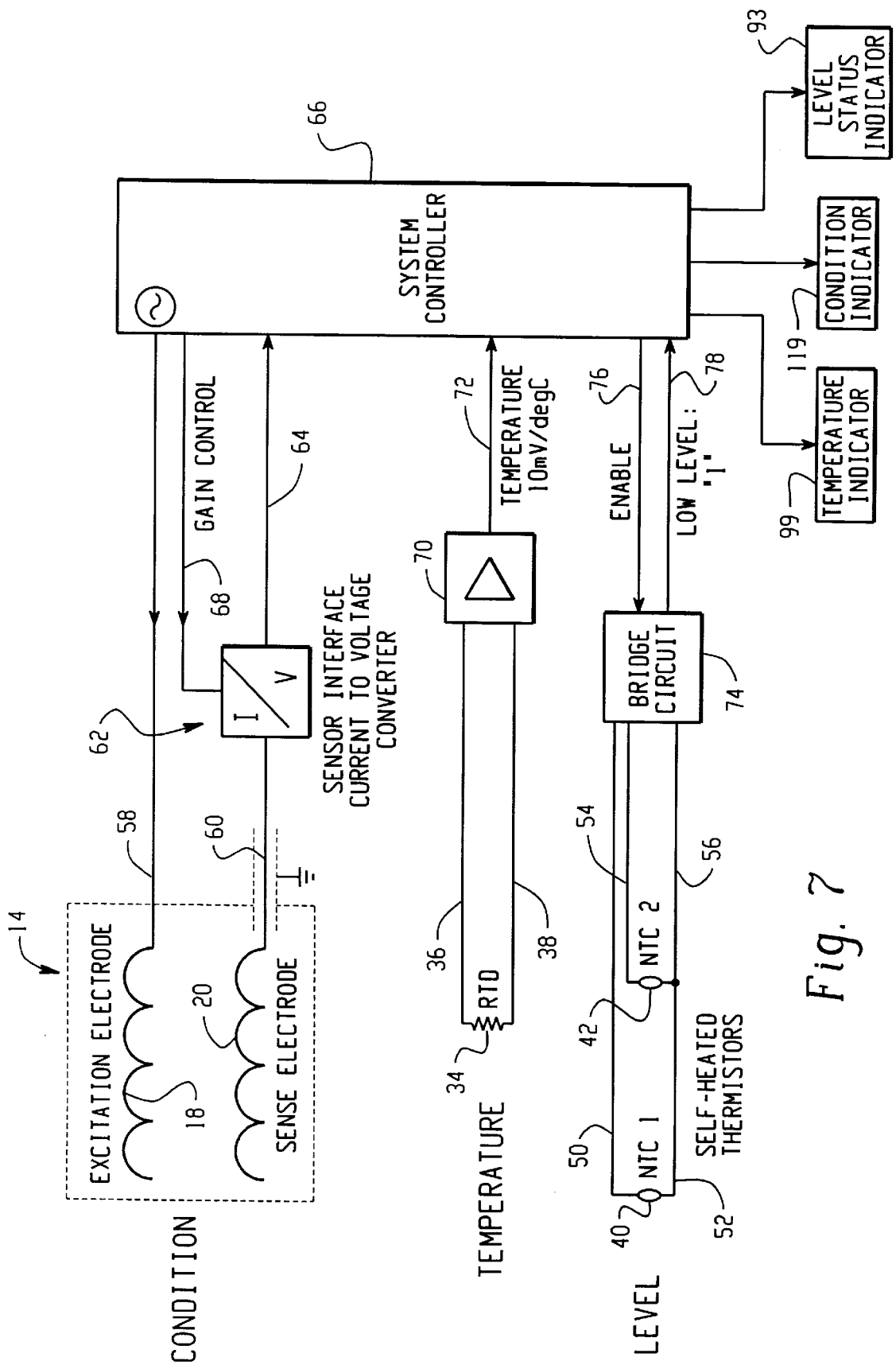
FIG. 7 is a block diagram of the electrical system of the monitor of FIG. 1.

Referring to FIG. 7, a block diagram of electrical system of the present invention 10 is illustrated wherein the detecting lead 60 from probe 14 is connected to the input of a current to voltage converter indicated generally at 62 which has its output on line 64 connected to the input of the system controller 66 which is of the type containing a microcomputer or a microprocessor. The remaining electrode lead 58 of probe 14 is connected to the excitation output of controller 66. The converter 62, as will be hereinafter described in greater detail converts the current through the probe electrodes, from a constant voltage excitation, to a voltage signal as an electrical analog of the probe impedance in the fluid. Alternative, the probe electrodes may be excited from a constant current supply and the voltage measured as an analog of impedance change. In the presently preferred practice, the probe electrodes are excited with a relatively low constant voltage of about 250 milli-volts. The current to voltage converter has a gain control input along line 68 from the controller 66. The temperature sensing RTD 34 has its leads 36, 38 connected to a signal conditioning amplifier 70, which provides an input along line 72 to the controller 66. The RTD in the present practice provides a signal level of about 10 milli-volts per degree C. The techniques for calibrating an electrical signal and determining temperature from an RTD are well known in the art and will not be discussed further herein for the sake of brevity.

The optional level sensing thermistors 40, 42 have their leads 50, 54, 56 connected to a Wheatstone bridge circuit 74 which is connected via lines 76, 78 to the controller.

Figure 8:
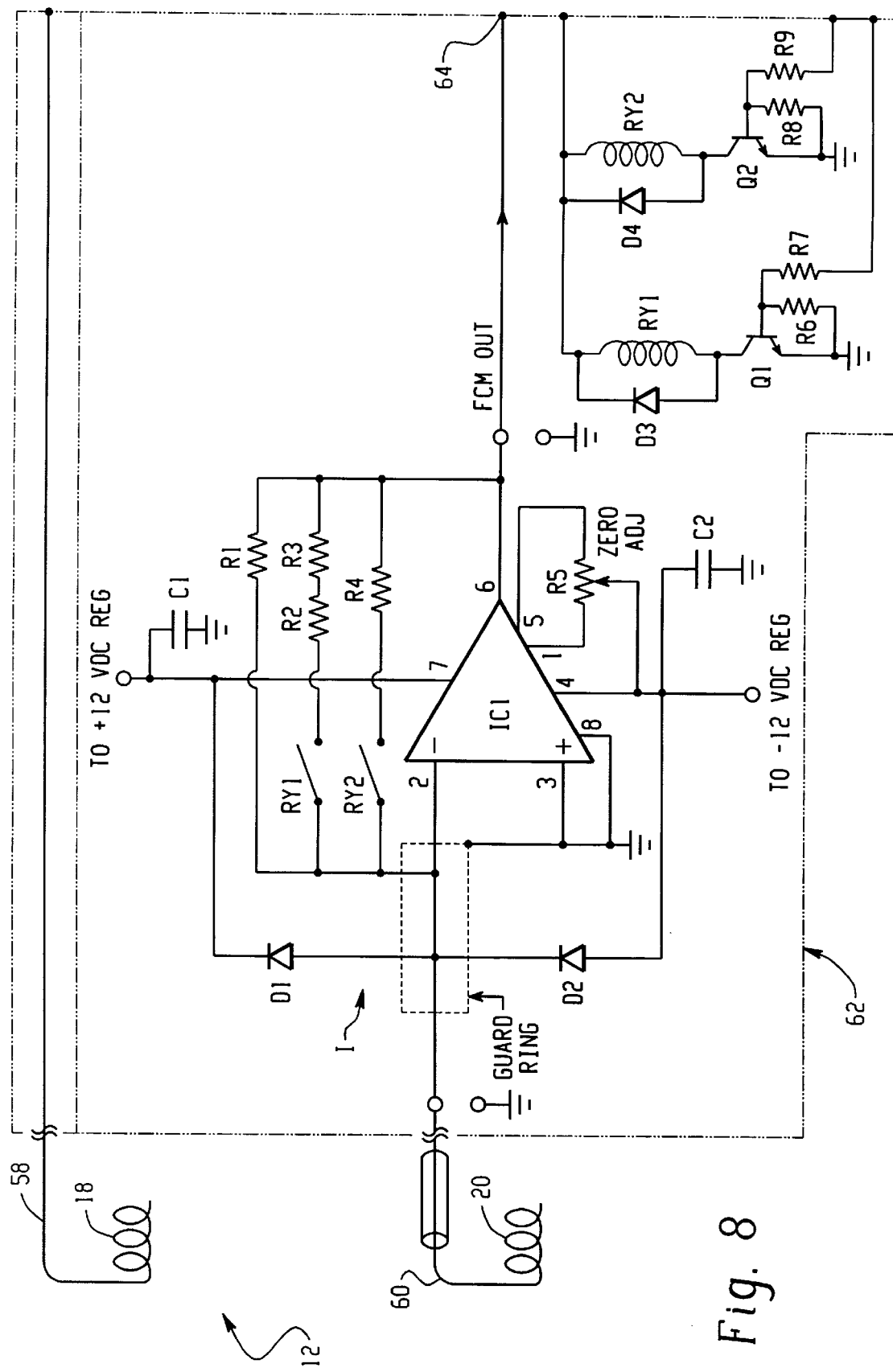
FIG. 8 is a circuit schematic of the current voltage converter of FIG. 7.

Referring to FIG. 8, a circuit schematic for the current to voltage converter 62 is illustrated wherein a sensitivity of 0.1 volt per nano ampere is determined by the resistor R1 in the feedback path from the output of IC1 with a secondary range providing a sensitivity of 0.01 volts per nano ampere through the resistor R2 and R3 upon closure of relay switch RY1. A sensitivity of 0.001 volts per nano ampere is obtained by closure of relay switch RY2 to include resistance R4 in the network.

Transistors Q1 and Q2 are used to drive the relay coils of RY1 and RY2; and, the base junctions of Q1 and Q2 are driven by logic signals from the controller 66 to provide autoranging for measurement of a wide range, for example, three decades, of current sensing. Values and designations for the circuitry components are given in Table I.

TABLE I

| Device | Type | Device | Type |
| --- | --- | --- | --- |
| R1 | 100 MEG | C1 | 0.1 $\mu f$ |
| R2 | 10 MEG | C2 | 0.1 $\mu f$ |
| R3 | 1.1 MEG | IC1 | OPA128; A549 |
| R4 | 1.1 MEG | Q1 | 2N 6426 |
| R5 | 50 K | Q2 | 2N 6426 |
| R6 | 10 K | D1 | 1N 4003 |
| R7 | 10 K | D2 | 1N4003 |
| R8 | 10 K | D3 | 1N4003 |
| R9 | 10 K | D4 | 1N4003 |
| RY1 | Relay Coil | | |
| RY2 | Relay Coil | | |

The controller 66 measures the current as an analog of the impedance of the electrodes 18, 20 in the fluid at a first low or fractional Hertz frequency and then at a frequency of at least one Hertz, and converts the current measurements to voltages. The measured currents are adjusted for temperature variaion from a known relationship of electrode current as a function of temperature and a subtraction is performed and then the differential value is compared with values stored in a look-up table to determine whether the differential impedance is below a critical value established for a known fluid condition. The technique for performing this operation is shown and described i n the aforesaid patent application Ser. No. 09/220,556 filed Dec. 23, 1998 incorporated herein and thus Will not be described in further detail insofar as the electrical circuitry arrangement for performing these signal processing and data reduction functions.

Referring to FIGS. 2, 3 and 7, fluid level detection is performed by self-heating thermistors 40, 42 and determining the resistance change thereof due to the presence of liquid or the lack of change due to the absence of liquid in a manner well known in the art.

Figure 9A:
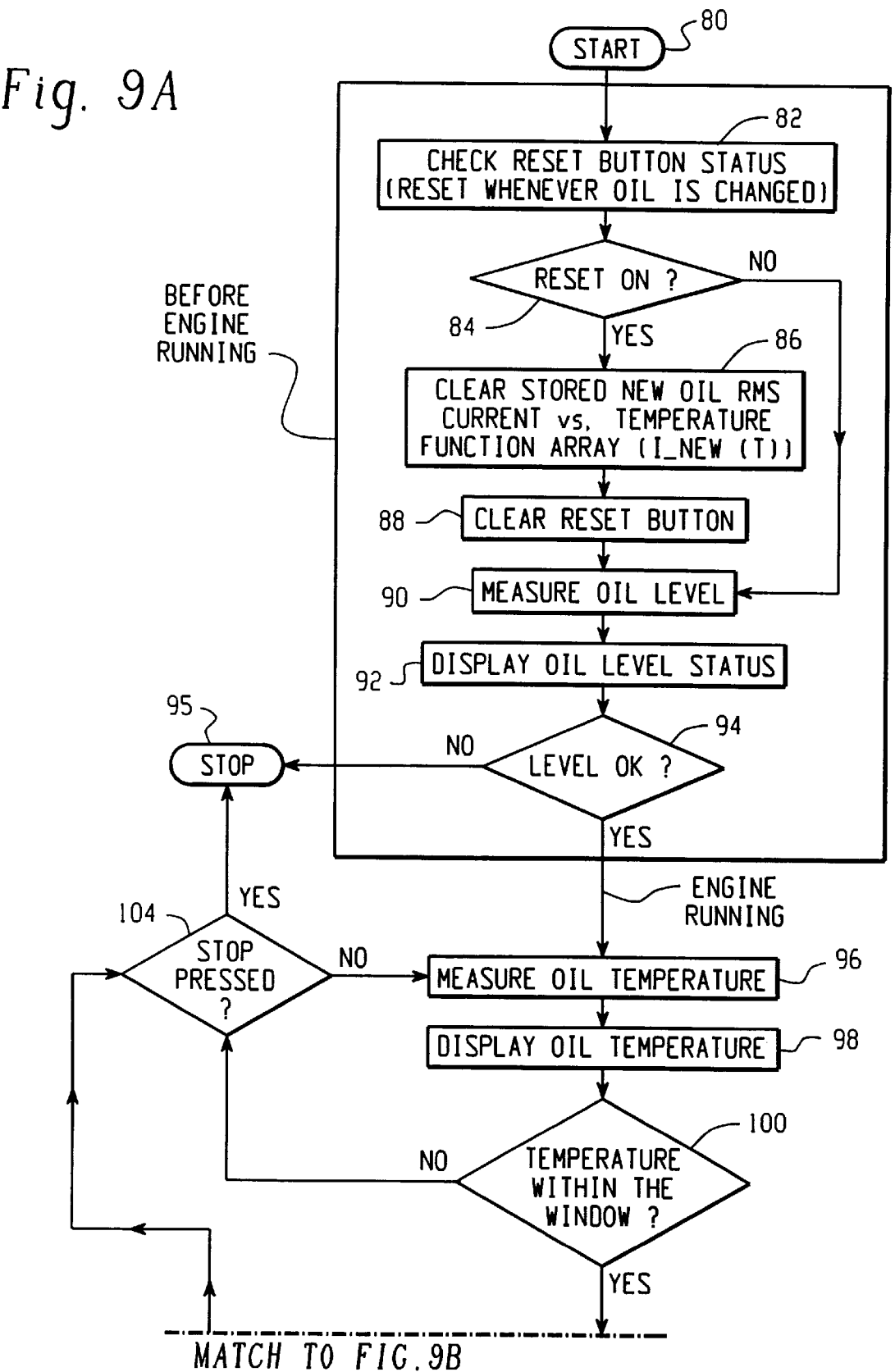
FIGS. 9A and 9B are a block flow diagram of the program for the microcomputer of the system of FIG. 7.
Figure 9B:
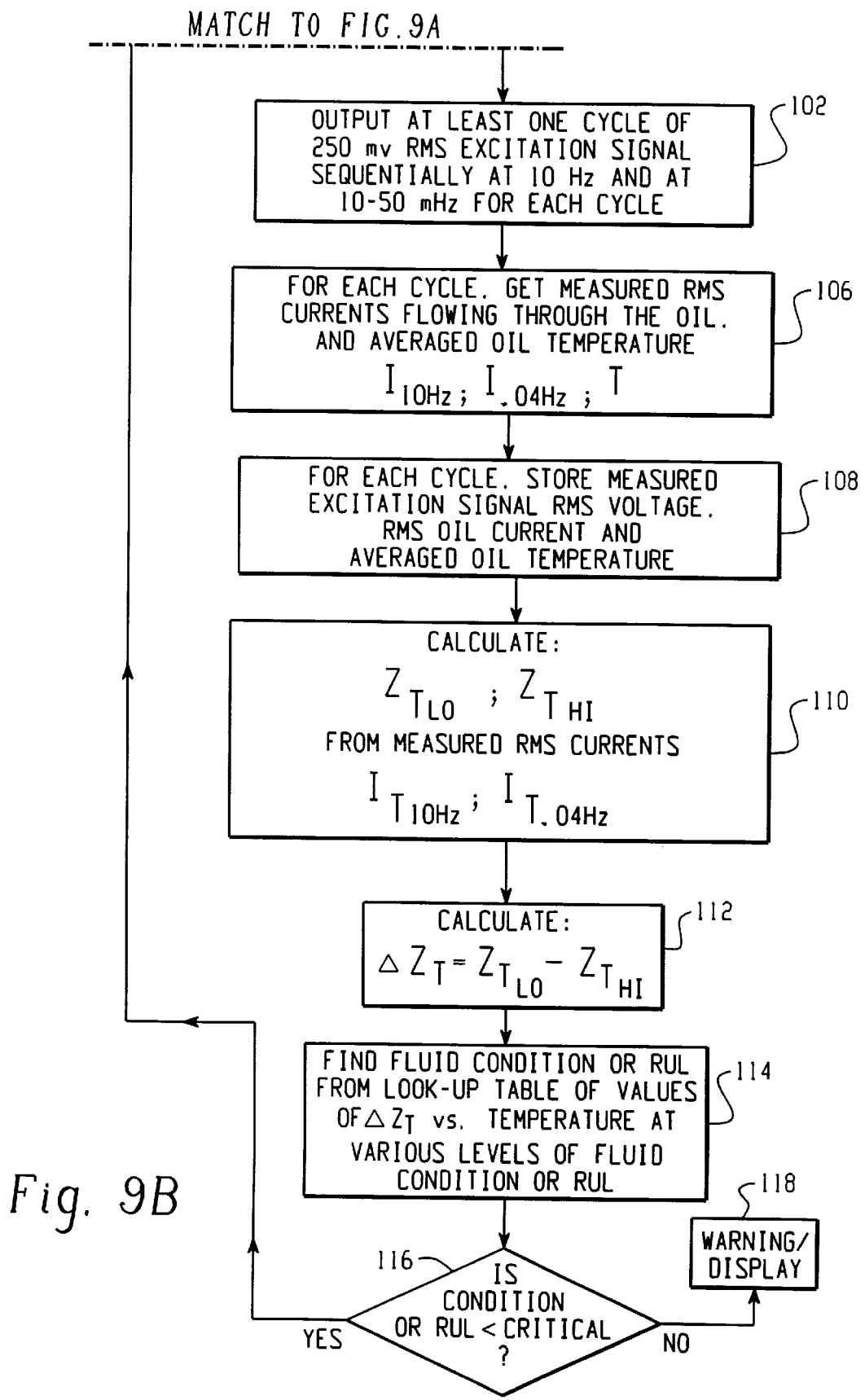

Referring to FIGS. 9A and 9B, the system operation for performing the method of the present invention will be described with reference to the flow diagram wherein a preliminary computation is performed upon system power up at step 80 and proceeds to check the Reset at step 82. The system proceeds to step 84 and makes a determination as to whether the Reset is on; and, if the answer is affirmative, the system proceeds to step 86 to clear the temperature function array and then proceeds to step 88 to clear the Reset button and proceeds to step 90 to measure the oil level with the energization of self-heating thermistors 40, 42. If however, the determination at step 84 is negative, the system proceeds directly to step 90 to measure the oil level.

The system proceeds to display the oil level status at step 92 which is shown by an indicator 93 in the diagram of FIG. 7.

Referring to FIGS. 9A and 9B, the system proceeds to step 94 and makes a determination as to whether the oil level is satisfactory and if the determination is affirmative proceeds to step 96 to measure oil temperature. It will be understood that the mechanical system employing the fluid such as engine oil is activated by starting the engine prior to step 96. If the determination at step 94 is negative, the system proceeds to shut down at step 95.

Referring to FIGS. 9A and 9B, the system proceeds to display the measured oil temperature at step 98 by using temperature indicator 99 shown in FIG. 7.

The system then proceeds to step 100 to make a determination as to whether the temperature is within a predetermined allowable range; and, if the determination at step 100 is affirmative the system proceeds to step 102 and applies the constant voltage excitation signal of about 250 milli-Volts to about 1 Volt RMS excitation to the probe electrodes 18, 20 sequentially at a high frequency in the range of about 1–100 Hertz, preferably 1–10 Hertz and then at a fractional or low-frequency in the range of about 10 to 50 milli-Hertz and preferably 40 to 50 milli-Hertz.

In the present practice of the invention, it has been found that a frequency of about 10 milli-Hertz for the low frequency optimizes sensitivity; whereas a frequency of about 100 milli-Hertz gives a faster response but diminished sensitivity. The measurements were taken for fluid in the temperature range of 60°–120° C. but at a relatively stabilized temperature as representative of engine operation after complete warm up.

If the determination at step 100 is negative, the system proceeds to step 104 to determine if a Stop button has been energized; and, if not the system returns to step 96. If the operator has pressed the Stop button the system proceeds to step 95 to shut down.

Upon the constant voltage excitation of the probe electrodes at step 102 sequentially at the two chosen frequencies, the system proceeds to step 106 and measures the current through the probe electrodes at each of the selected frequencies of excitation and proceeds to step 108 to store the measured currents (converted to voltage) and the average fluid temperature. The system then proceeds to step 110 and computes the impedance from the measured RMS currents $I_L$, $I_H$ at the averaged temperature $T_F$. The difference in the impedance $\Delta Z_T$ is then computed at step 112.

Figure 10:
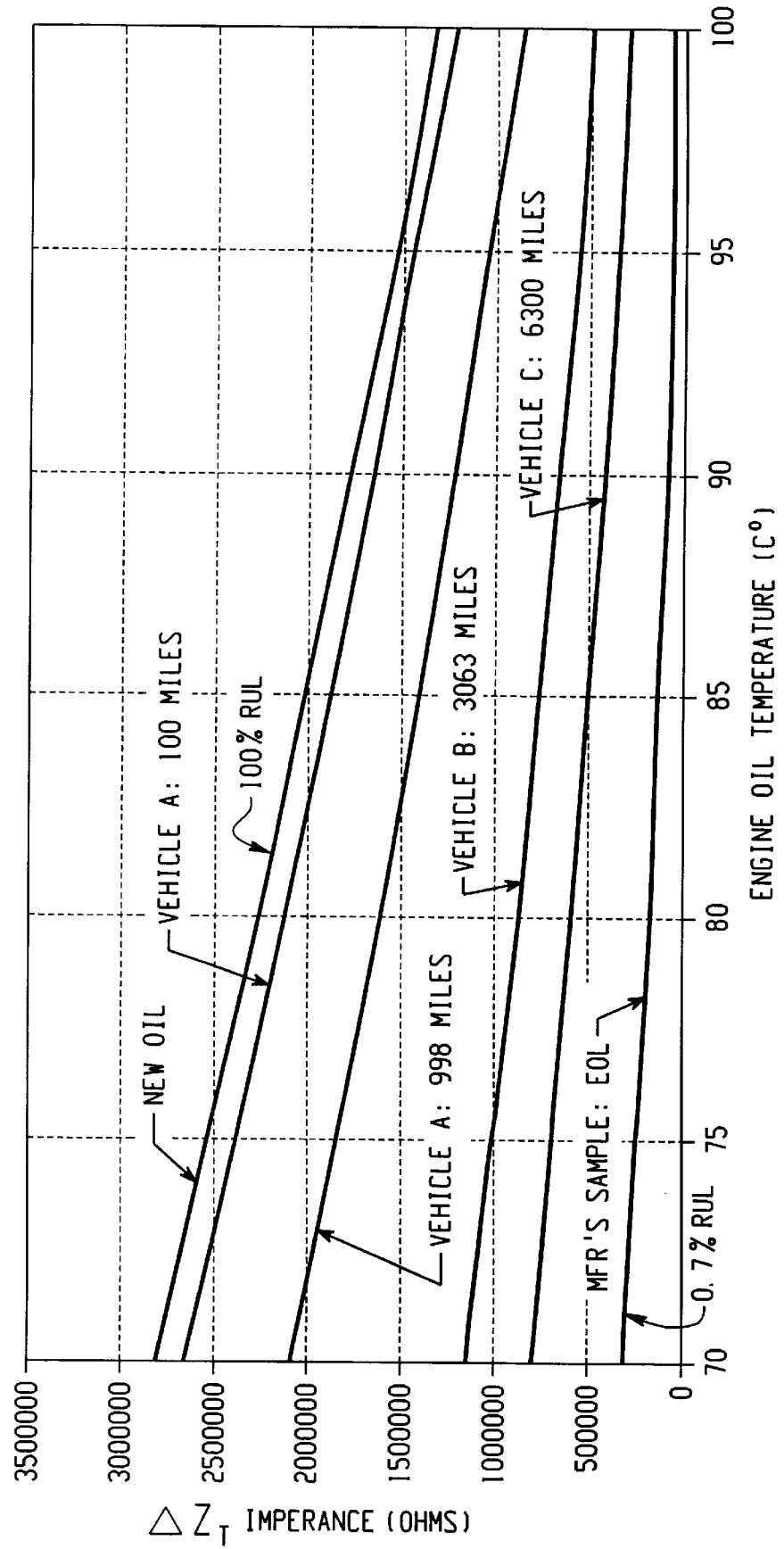
FIG. 10 is a graph of the differential impedance $\Delta Z$ from the procedure of FIG. 9 for the probe of FIGS. 1 through 4 plotted as a function of temperature for synthetic engine drain oil taken from a first and second vehicle at different mileage intervals.

Referring to FIG. 10, typical curves are presented for measurements of engine oil at various temperatures plotted as a function of the differential impedance $\Delta Z_T$. The system then proceeds to step 114 and finds the fluid condition or RUL from a lookup table of the value of $\Delta Z_T$ as a function of temperature for various levels of fluid condition or percentages of RUL. It will be understood that the lookup table may be compiled from the data points of the curves of FIG. 10. Step 114 may be performed either by entering the graph of FIG. 10 at the $\Delta Z_T$ from step 112 for the average temperature $T_F$ stored in step 108 and finding the fluid condition or RUL by interpolation; or, an equation may be fitted to the curves by any of the known curve fitting techniques such, as for example, multiple regression analysis. In the present practice of the invention curve fitting techniques have been employed to the data in FIG. 10 provide the expressions for $\Delta Z_T$ as follows:

For synthetic PCMO:

$$\Delta Z_{T\ NEW} = 8.106 \times 10^6 - 9.3 \times 10^4 T + 256 T^2$$

$$\Delta Z_{T100} = 8.966 \times 10^6 - 12 \times 10^4 T + 428 T^2$$

$$\Delta Z_{T998} = 8.063 \times 10^6 - 11.7 \times 10^4 T + 452 T^2$$

$$\Delta Z_{T3063} = 4.46 \times 10^6 - 6.48 \times 10^4 T + 250 T^2$$

$$\Delta Z_{T6300} = 3.24 \times 10^6 - 4.72 \times 10^4 T + 175 T^2$$

$$\Delta Z_{TEOL} = 2.95 \times 10^6 - 5.73 \times 10^4 T + 284 T^2$$

The system then proceeds to step 116 to make a determination as to whether the fluid condition or RUL computed in step 114 is less than a critical value; and, if the determination is positive, the system returns to step 104. However, if the system determination at step 116 is negative, the system proceeds to display a warning at step 118 which signals the condition indicator 119 in FIG. 7.

The present invention thus provides a technique for determining the condition of a fluid such as, for example, engine oil on a running basis during engine operation, by computing values of impedance from current measurement taken with constant voltage excitation sequentially at the high and fractional Hertz or low frequencies and subtracting the temperature corrected values to determine a differential of the current (converted to voltage) as an analog of the change in impedance of the electrodes immersed in the fluid. The electrical analog of the differential of measured impedance at the two selected frequencies may then be compared with values of the impedance differentials as a function of temperature for known fluid conditions in a look-up table to determine whether the signal indicates a fluid condition less than a pre-selected or critical condition.

The signal processing and data reduction techniques of the present invention are described and illustrated herein as employed with a spirally wound capacitive probe comprising a pair of spaced helically wound wires; however, it will be understood that the electrical signal processing techniques as described may also be employed to FIGS. 8 and 9 with a parallel plate capacitive probe or interdigitated electrode probe as described in the aforesaid copending Bauer, et al. application Ser. No. 09/220,556 filed Dec. 23, 1998 and incorporated herein by reference.

Although the present invention computes the differential of impedances from the current measured at the low and high frequencies, it is to be understood that alternatively the phase angle of the excitation voltage and the resultant current may be measured; and, the difference, or phase shift may be computed and compared with a table of known values as a function of temperature for various fluid conditions as an analog of reactive impedance change; and, is thus a means or way of determining the condition of the monitored fluid employing the technique of the present invention.

Figure 11:
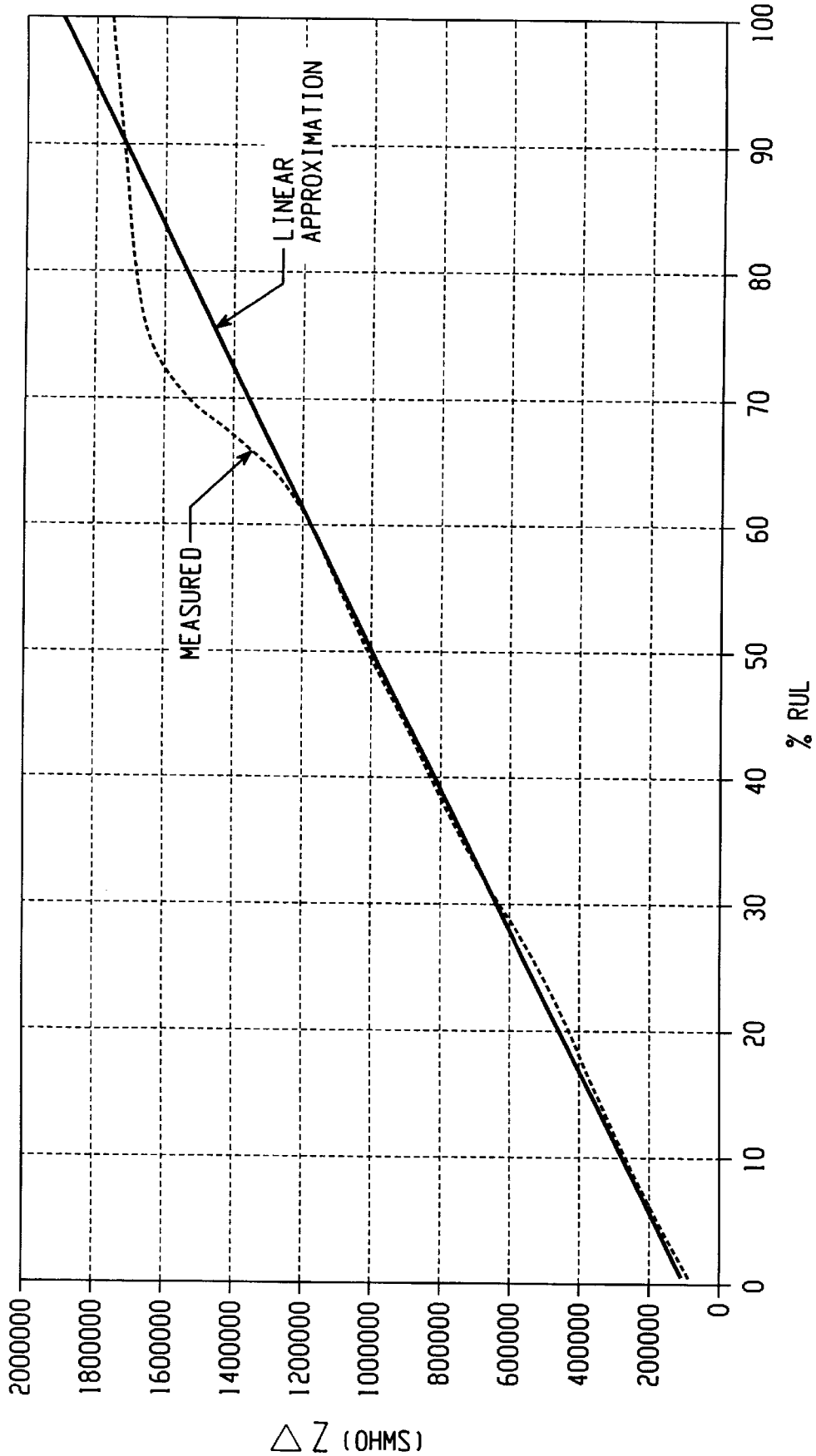
FIG. 11 is a graph of differential impedance valves plotted as a function of percent Remaining Useful Life (RUL) for 5W-30 and 10W-30 synthetic oil at different vehicle mileages for several vehicles.

Referring to FIG. 11, values of the difference of the impedance $\Delta Z$ measured employing the technique of FIGS. 8 and 9 at the high and low frequencies taken for samples of used passenger car motor oil (PCMO) are plotted as a function of the percent remaining useful life (RUL) of the oil in graphical form. The basis for end of remaining useful life is a known sample of oil provided by an engine oil manufacturer and designated by the oil manufacturer as at the "end of useful life" (EOL) based upon the oil manufacturers chemical analysis. The basis for 100% useful remaining life are the measurements taken from new engine oil of the same type. If these assumed boundary conditions are connected by a straight line plot, impedance measurements taken with the probe of the present invention may be entered on the straight line plot graph of FIG. 11 to determine the remaining useful life. It will be understood that FIG. 11 is based on impedance measurements performed in accordance with the present invention on SAE 5W-30 and SAE 10W-30 viscosity rated synthetic passenger car motor oil (PCMO).

Thus it will be seen that the in situ running impedance measurements taken in accordance with the present invention and utilizing the techniques shown and described herein may be used in real time to provide an indication of remaining useful life (RUL) which can be electrically displayed to the vehicle operator. Alternatively, the electrical indication may simply be provided when the oil condition has reached a predetermined critical state wherein the operator can be notified to change the engine oil before continuing operation.

The spiral probe arrangement of the present invention shown in FIGS. 1 through 4 is particularly suitable for sizing and configuring so as to be insertable in an existing dipstick hole provided in an engine; and, thus the probe assembly of the present invention may be retrofitted on existing engines without any modification of the engine.

Figure 12:
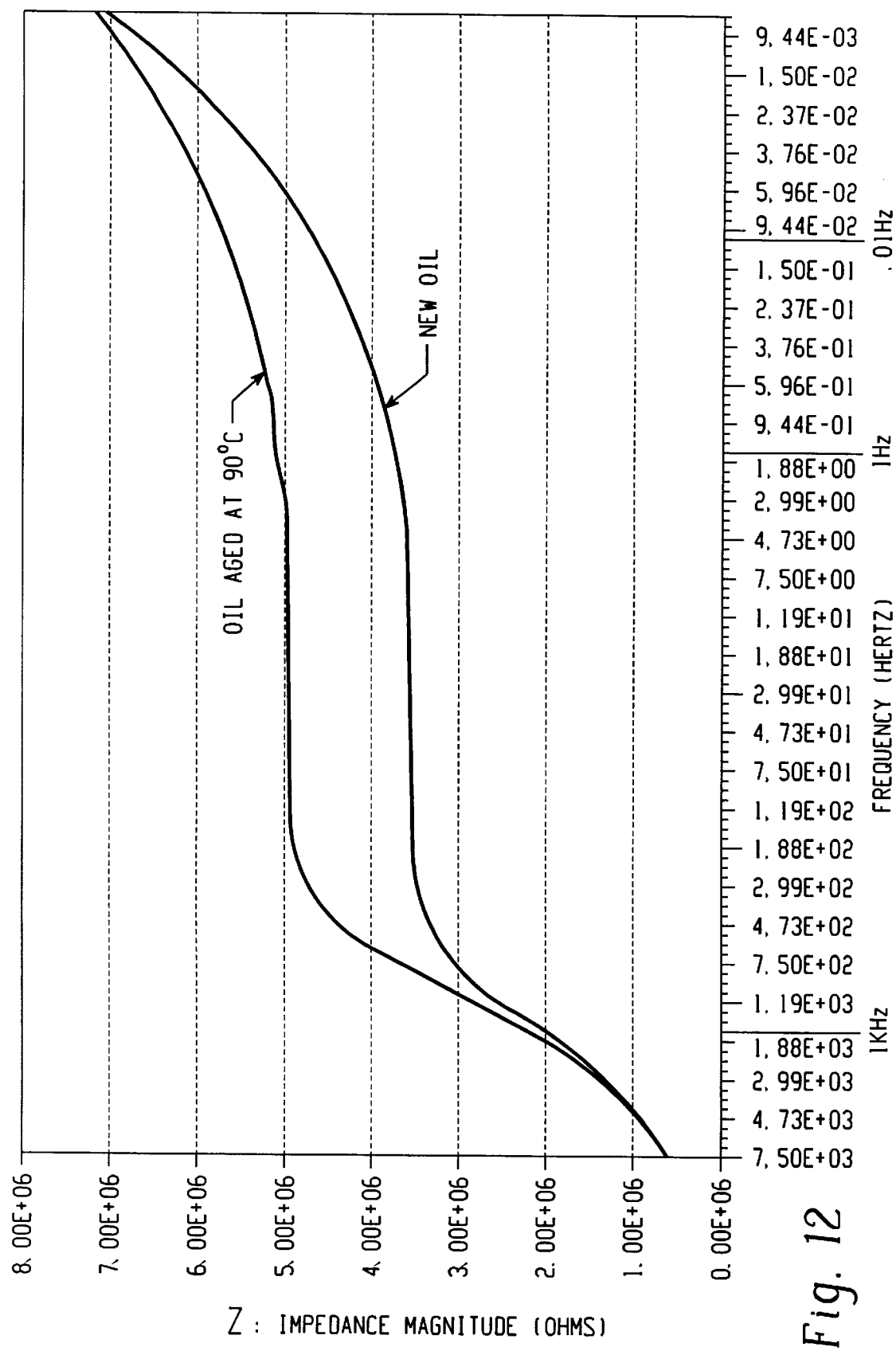
FIG. 12 is a graph of measured impedance $\Delta Z$ plotted as a function of frequency of excitation for a spiral probe and calculations according to FIGS. 8 and 9.

Referring to FIG. 12 the impedance Z measured in accordance with the technique of FIG. 9 for excitation at 250 milli-Volts are plotted as a function of frequency at frequencies of excitation current ranging from 1 milli-Hertz to 10 kHz for new and temperature aged synthetic PCMO measured with a spiral probe in accordance with FIGS. 1–4. From FIG. 12, it will be seen that after excitation at a first frequency of 10–100 Hertz and at a second frequency of from 10 to 50 milli-Hertz, the difference in impedance is quite sufficient to give the resolution needed to provide an indication of the change in fluid properties; and, thus the spiral probe of FIGS. 1 through 4 is considered to be a practical alternative to the parallel interdigitated electrode probe described in the aforesaid co-pending Bauer, et al. application Ser. No. 09/220,556 for real time monitoring of engine oil.

Figure 13A:
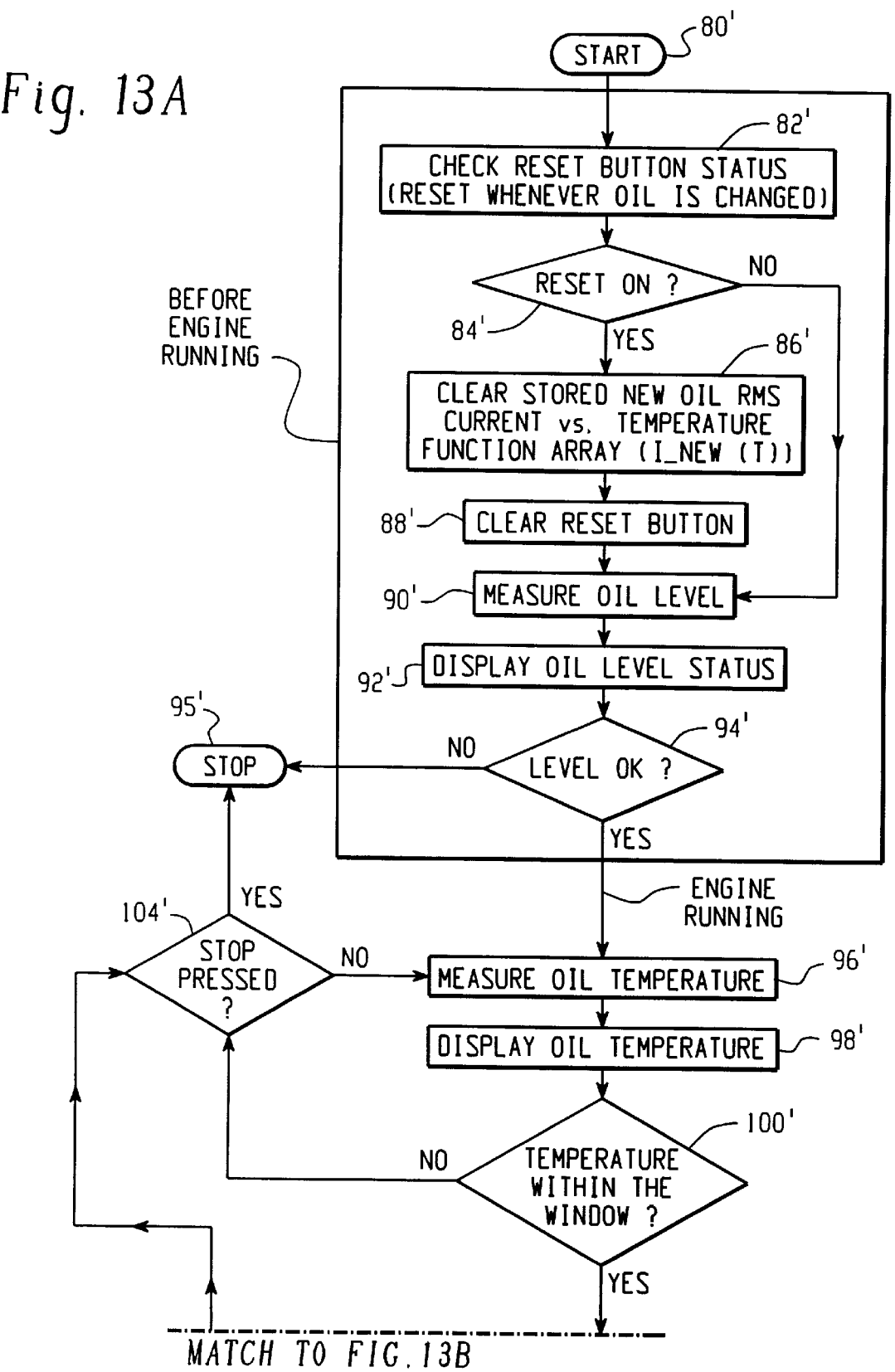
FIGS. 13A and 13B are a block flow diagram of an alternate program for the microcomputer of FIG. 7; and, FIG. 14 is a graph of values of differential reactance $\Delta Z_i$ plotted as a function of temperature for measurements taken with a spiral probe and calculations according to FIG. 13 for synthetic engine drain oil accumulated for a first and second vehicle at different mileages.
Figure 13B:
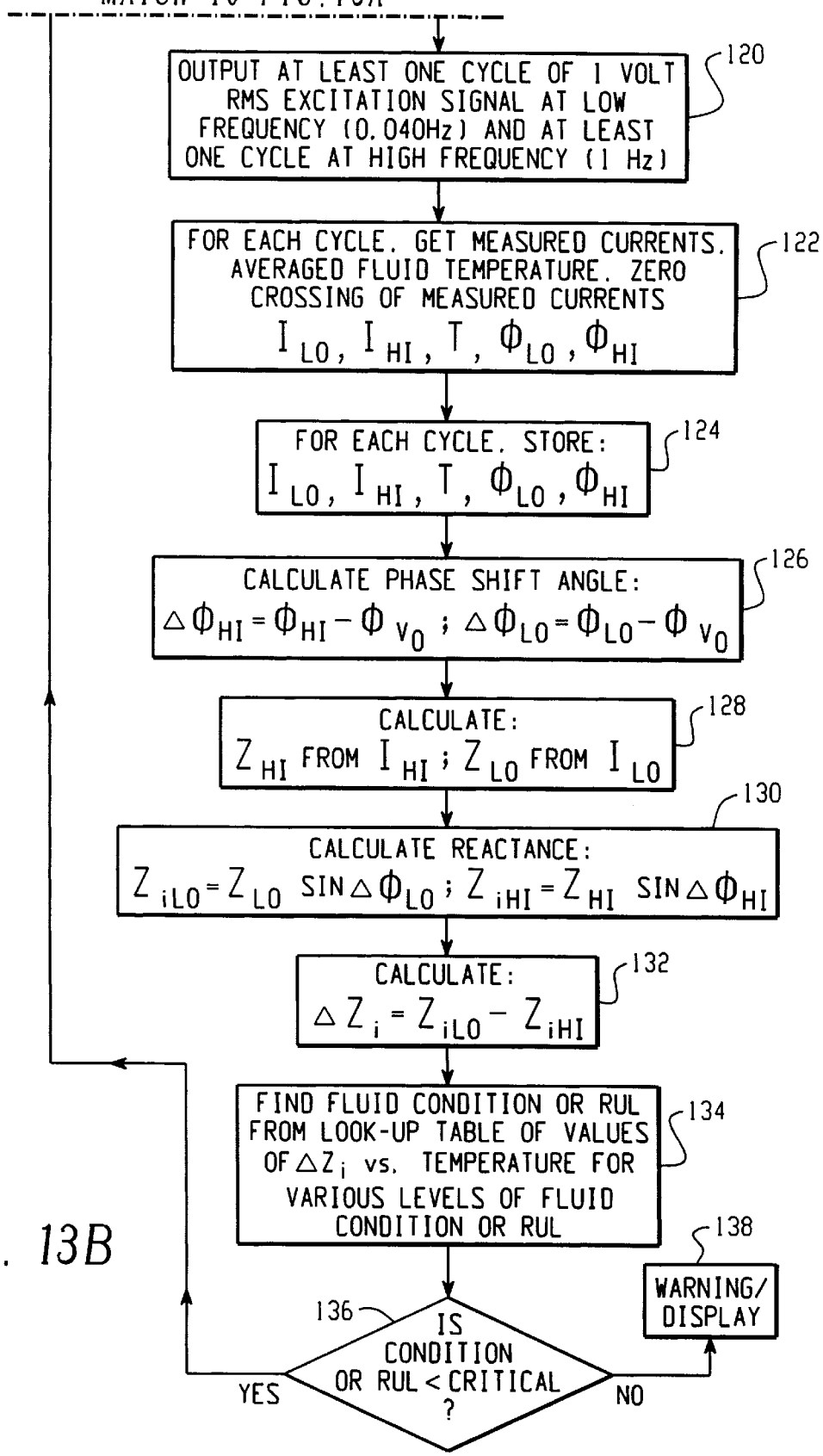

Referring to FIGS. 13A and 13B, an alternative technique for operating the system of FIG. 7 is illustrated in the form of a block flow diagram for the program of the microcomputer of FIG. 7. It will be understood that in the diagram of FIGS. 13A and 13B, those functions which are identical to those of FIG. 9 have been denoted with a similar reference numeral with a prime added.

The alternative program of FIGS. 13A and 13B causes the system of FIG. 7 to proceed from step 100' to step 120 wherein the output of at least one cycle of the one Volt RMS excitation signal at 0.040 Hertz and at least one cycle excitation of one Volt RMS at 1 Hertz is received by the microcontroller; and, the system proceeds to step 122 where the zero crossing of the current is detected; and, the zero crossing and average oil temperature both are stored at step 124.

The system then proceeds to step 126 and the phase angle shift $\Delta\Phi_{HI}$ and $\Delta\Phi_{LO}$ are computed from the stored zero crossings of step 122 and comparison with the zero crossing of the excitation voltage $V_O$. The system then proceeds to step 128 where values of the impedances $Z_{HI}$, $Z_{LO}$ are computed from the measured currents $I_{HI}$, $I_{LO}$.

The system then proceeds to step 130 where the capacitive reactance $Z_{iLO}$, $Z_{iHI}$ are computed from the phase angle shifts $\Delta\Phi_{LO}$, $\Delta\Phi_{HI}$, respectively from step 126.

The system then proceeds to step 132 and calculates the change in capacitive reactive $\Delta Z_i$ from the values of reactance computed in step 130. The system then proceeds to step 134 and finds, from a lookup table the values of $\Delta Z_i$ versus temperature for various levels of fluid condition, the present condition or RUL of the fluid measured at the computed $\Delta Z_i$ and measured temperature. The system then makes a determination at step 136 whether the fluid condition or RUL is less than a pre-selected critical level or RUL; and, if the result is affirmative, the system returns to step 104'. If the determination at step 136 is negative, the system proceeds to step 138 and provides a warning or display.

Figure 14:
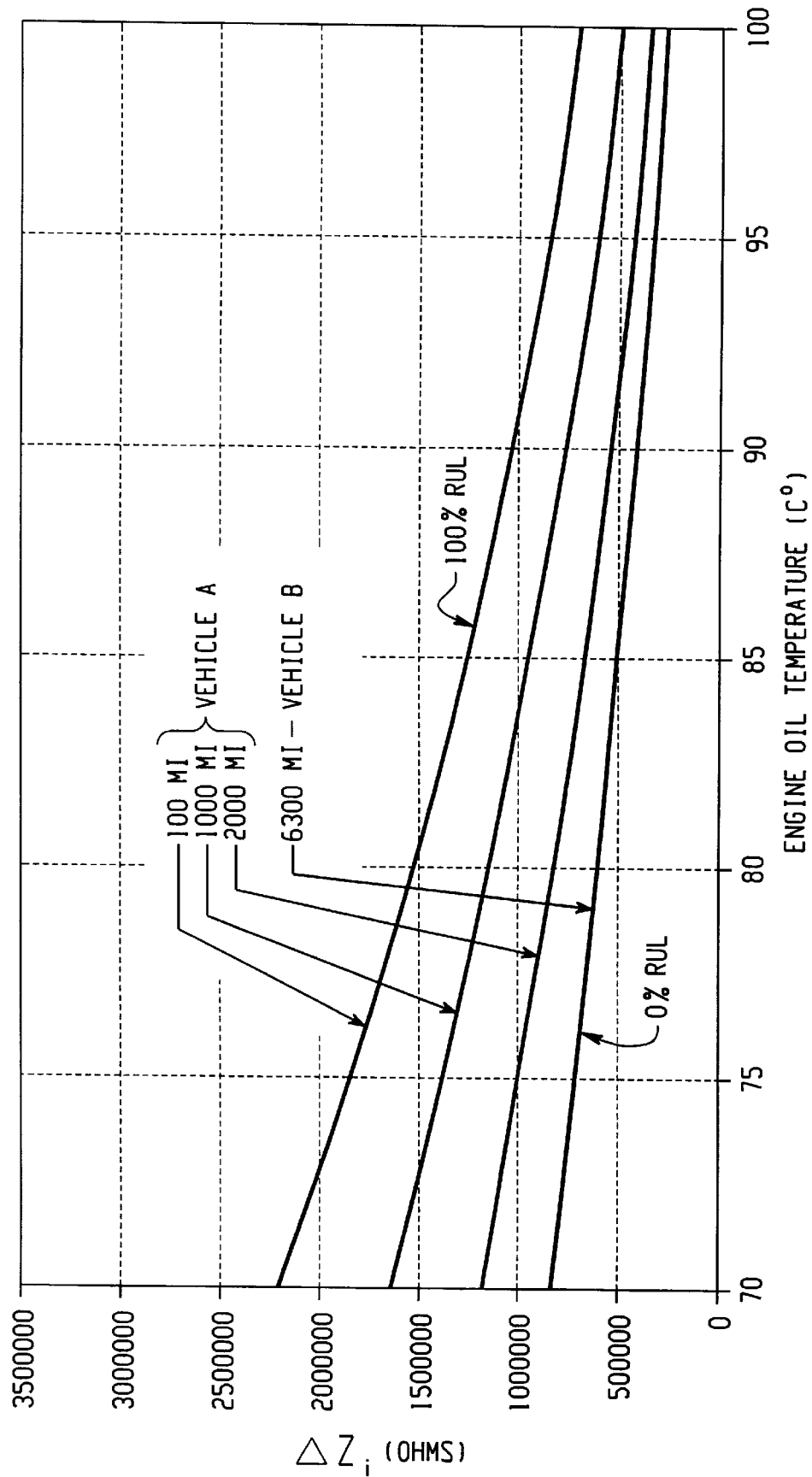

Referring to FIG. 14, values of $\Delta Z$ in ohms are plotted as a function of oil temperature in degrees Centigrade for samples of 5W-30 synthetic motor oil as measured with a wire wound probe at 1 Volt RMS excitation at 10 Hertz and 100 milli-Hertz frequency for vehicles at different oil drain intervals. In FIG. 14, 100% RUL has been assigned to the upper curve for 100 mile drain oil; and, zero percent has been assigned to the lowest curve for 6300 mile drain oil.

It will be understood that the values of fluid condition or RUL are found by interpolation from FIG. 14 by entering the graph at the temperature stored in step 122 and the value of $\Delta Z_i$ computed in step 132 of the procedure of FIG. 13. Alternatively, the fluid condition or RUL for the temperature T stored at step 122 and $\Delta Z_i$ computed at step 132 may be interpolated from values computed from the following expressions derived by curve fitting techniques to the graphs of FIG. 14:

$$\Delta Z_{i100} = 12.0 \times 10^6 - 202 \times 10^3 T + 8.90 T^2$$

$$\Delta Z_{i100} = 8.16 \times 10^6 - 131 \times 10^3 T + 548 T^2$$

$$\Delta Z_{i200} = 6.49 \times 10^6 - 109 \times 10^3 T + 473 T^2$$

$$\Delta Z_{i6300} = 3.74 \times 10^6 - 56.8 \times 10^3 T + 221 T^2$$

It will be seen from the upward shift of the plots of FIG. 14, as the mileage of the vehicle is increased, the drain samples, tested by the spiral probe of the present invention, indicate an almost uniform shift over the temperature range for the phase angle shift. Thus it will be seen that from FIG. 14, the percentage remaining useful life of the engine may also be determined with the probe in the present invention using the alternative program of FIG. 13.

The invention has been described in great detail in the foregoing specification; and, it is believed that various alterations and modifications of the invention will become apparent to those skilled in the art from a reading and understanding of the specification. It is, therefore, intended that all such alterations and modifications are included in the invention, insofar as they come within the scope of the following claims.

What is claimed is:

1. A fluid condition sensor for insertion in an aperture in a fluid filled vessel comprising:
   (a) an elongated member having a distal end and a proximal end and including certain surfaces with a relatively low dielectric constant;
   (b) a pair of electrically conductive members disposed on said certain surfaces in spaced spiral arrangement adjacent said distal end, each member of said pair having an electrical lead extending to said proximal end;
   (c) electrical circuitry associated with the proximal end of said elongated member and operatively connected to said leads, said circuitry operable to measure the electrode surface impedance between said pair at a first (low) frequency and to measure the bulk fluid impedance at a second (high) frequency of at least one Hertz and compute the difference and compare the difference with predetermined values and determine the fluid condition.

2. The sensor defined in claim 1, wherein said pair of conductors are spirally interdigitated.

3. The sensor defined in claim 1, wherein said rod member has helical grooves formed thereon with said pair of conductors received in said grooves.

4. The sensor defined in claim 1, wherein said rod member has a hollowed configuration.

5. The sensor defined in claim 1, wherein said elongated member includes a casing disposed thereover in the region of said proximal end with said circuitry disposed in said casing.

6. The sensor defined in claim 1, wherein said elongated member includes a casing disposed thereover in the region of said proximal end, said casing including a seal for sealing about said vessel aperture.

7. The sensor defined in claim 1, wherein said elongated member includes a pair of resistors spaced therealong and said circuitry is operable for determining the change in resistance of said resistors for determining the level of fluid in said vessel.

8. The sensor defined in claim 1, wherein said pair of conductors are helically wound as a pair on said elongated member.

9. The sensor defined in claim 1, further comprising means operable for removably sealing said elongated member in said aperture.

10. A method of continuously monitoring the condition of fluid in a vessel having an aperture for a dipstick comprising:
    (a) providing an elongated member of relatively low permittivity having a distal and proximal end and disposing a pair of generally spirally arranged spaced electrical conductors thereon in the region of the distal end;
    (b) disposing electrical circuitry on said elongated member in the region of the proximal end and connecting said circuitry to said pair of conductors and inserting said distal end through said aperture into said fluid and detecting the bulk fluid impedance between said conductors at a first frequency (low) and detecting the electrode surface impedance at a second (high) frequency of at least one Hertz; and, (c) computing the difference in said detected impedances and comparing said difference with predetermined values for said fluid and determining the condition of said fluid and providing an electrical indication when a certain fluid condition exists.

11. The method defined in claim 10, wherein said step of disposing a pair of spaced conductors includes spirally winding said conductors on said elongated member.

12. The method defined in claim 10, wherein said step of disposing said electrical circuitry including disposing a casing in the region of proximal end of said elongated member and disposing said circuitry in said casing.

13. The method defined in claim 10, further comprising:
(a) disposing a pair of thermistors in the region of the distal end of said elongated member and connecting said thermistors to said circuitry and self heating said thermistors and determining the level of said fluid in said vessel.

14. The method defined in claim 13, wherein said step of disposing said pair of conductors includes winding said conductors in a pair of spiral grooves formed on said elongated member.

15. The method defined in claim 10, wherein said step of detecting the impedance change includes converting a current in said electrodes to a voltage.

16. The method defined in claim 10, further comprising:
(a) disposing an indicator remotely from said vessel; and,
(b) connecting said circuitry to said indicator and energizing said indicator when said impedance reaches a pre-determined value.

17. The method defined in claim 10, wherein said step of inserting said distal end of said elongated member through said aperture includes inserting said distal end into the lubricant sump of an internal combustion engine.

18. The method defined in claim 10, wherein said step of inserting said distal end through said aperture includes inserting said distal end through an aperture in the casing of a power transmission lubricant reservoir.

19. A removable fluid condition monitor for insertion through a dipstick aperture in a fluid reservoir comprising:
(a) an elongated member of relatively low permittivity having a distal end for insertion through said aperture and a proximal end for remaining exteriorly disposed with respect to said reservoir;
(b) a pair of electrical conductors disposed in spaced generally parallel spiral relationship on said member in the region of the distal end;
(c) a casing structure associated with the proximal end of said member; and,
(d) circuitry disposed within said casing and connected to said conductors and operative to determine the electrode surface impedance between said conductors at a first (low) frequency and to determine the bulk fluid impedance at a second (high) frequency of at least one Hertz, said circuitry including a computer operable to compute the difference in said impedances and compare the difference with predetermined values for various conditions of the fluid and further operable to provide an electrical indication when said comparison correlates with a certain of said conditions.

20. The monitor defined in claim 19, wherein said elongated member has a hollow tubular configuration.

21. The monitor defined in claim 19, wherein said pair of conductors is wound in a spirally interdigitated arrangement on said member.

22. The monitor defined in claim 19, further comprising an indicator operable in response to said electrical indication to provide a humanly perceptible signal that said certain value has been reached.

23. The monitor defined in claim 22, wherein said indicator is disposed remotely from said casing structure.

24. The monitor defined in claim 19, wherein said pair of conductors are disposed in helical arrangement having a first portion at a first pitch and a second portion at a second pitch of about half the first pitch.

25. The monitor defined in claim 19, wherein said pair of conductors are disposed in about thirteen turns at 0.011 inch (0.28 mm) pitch and about eight turns at 0.032 inch (0.81 mm) pitch.

26. The monitor defined in claim 19, wherein said elongated member is formed of material selected from the group polytetrafluoroethylene (PTFE) and polyphenylsulfide.

27. The monitor defined in claim 19, wherein said elongated member has a transverse dimension of about 0.25 inch (6.3 mm).

28. The monitor defined in claim 19, wherein said pair of conductors are formed of wire having a diameter of about #25 AWG (0.46 mm).

29. The monitor defined in claim 19, wherein said pair of conductors are formed of Iron-Nickel-Chromium alloy material having a relatively low magnetic permeability.

30. The monitor defined in claim 19, wherein said pair of conductors are wound in spiral grooves formed in said elongated member.

31. The monitor defined in claim 19, wherein said pair of conductors are formed of wire having a generally rectangular cross section.

32. A method of monitoring fluid condition in real time comprising:
(a) immersing a pair of closely spaced electrodes in said fluid and connecting said electrodes to a source of electrical current;
(b) flowing a fractional ampere alternating current through said electrodes at a relative low voltage sequentially at a first frequency of at least one Hertz and at a second frequency less than said first frequency and measuring the current at said first and second frequency and computing the bulk fluid impedance from said first frequency current and the surface electrode impedance from said second frequency current;
(c) measuring the temperature of said fluid and storing said measured temperature;
(d) subtracting said impedance at said second frequency from said impedance at said first frequency and storing the differential;
(e) comparing said stored differential with valves of said differential at said stored temperature for known fluid conditions at said temperature; and,
(f) providing an electrical indication when said stored differential is less than a predetermined value for critical fluid condition.

33. The method defined in claim 32, wherein said step of flowing a current includes flowing said current at a first frequency of about 1–100 Hz and a second frequency of about 10–50 milli-Hz.

34. The method defined in claim 32, wherein said step of immersing includes disposing said electrodes in a spiral arrangement.

35. The method defined in claim 32, wherein said step of flowing current includes flowing said current at a first frequency of about 10 Hz and a second frequency of about 10 milli-Hertz.

36. A method of monitoring in real time the condition of a fluid in a vessel comprising:
   (a) disposing a pair of spaced generally parallel electrodes in the fluid to be monitored;
   (b) exciting said electrodes with an alternating generally constant voltage at a first frequency of at least one Hertz and at a second frequency less than said first frequency;
   (c) detecting the phase angle of the current in said electrodes resulting from said alternating voltage excitation;
   (d) comparing the phase shift angle of said current at said first and second frequency with the phase angle of said alternating voltage and computing the phase shift of said current at said first and second frequency;
   (e) computing the reactance from said phase shift angle and subtracting the reactance computed at said first frequency from the reactance computed at said second frequency;
   (f) determining the condition of the fluid with said reactance difference from known values of fluid condition and reactance difference for said fluid; and,
   (g) providing an electrical signal indicative of said fluid condition.

37. The method defined in claim 36, wherein said step of providing an electrical indication includes comparing said determined fluid condition with a predetermined threshold and indicating electrically if said threshold has been reached.

38. The method defined in claim 36, wherein said step of detecting the phase angle of said current includes detecting the zero crossing of said current.

39. The method defined in claim 36, wherein said step of exciting said electrodes with an alternating voltage includes exciting said electrodes with a voltage having a fractional Hertzian frequency in the range 10–100 milli-Hertz.

40. The method defined in claim 36, wherein said step of disposing a pair of electrodes includes disposing said electrodes in spiral arrangement.

* * * * *